United States Patent
Laursen et al.

(10) Patent No.: US 10,603,661 B2
(45) Date of Patent: Mar. 31, 2020

(54) MINI-FLUIDICS CASSETTE FOR COLORIMETRIC NUTRIENT ANALYSIS AND A METHOD OF USING SAME

(71) Applicant: NARWHAL ANALYTICAL CORPORATION (ONTARIO CORPORATION NUMBER 002408580), Stoney Creek (CA)

(72) Inventors: Andrew Laursen, Stoney Creek (CA); Christopher Bentley, Toronto (CA); Bahar Ameri, Toronto (CA)

(73) Assignee: Narwhal Analytical Corporation, Stoney Creek (CA)

( * ) Notice: Subject to any disclaimer, the term of this patent is extended or adjusted under 35 U.S.C. 154(b) by 465 days.

(21) Appl. No.: 15/506,261

(22) PCT Filed: Aug. 26, 2014

(86) PCT No.: PCT/CA2014/050818
§ 371 (c)(1),
(2) Date: Feb. 24, 2017

(87) PCT Pub. No.: WO2016/029288
PCT Pub. Date: Mar. 3, 2016

(65) Prior Publication Data
US 2017/0239655 A1 Aug. 24, 2017

(51) Int. Cl.
*B01L 3/00* (2006.01)
*B01F 5/06* (2006.01)
(Continued)

(52) U.S. Cl.
CPC ...... *B01L 3/502715* (2013.01); *B01F 5/0647* (2013.01); *B01F 13/0059* (2013.01);
(Continued)

(58) Field of Classification Search
CPC .......... B01L 3/502715; B01L 2200/12; B01L 2400/0487; B01L 2300/0883;
(Continued)

(56) References Cited

U.S. PATENT DOCUMENTS

| | | | |
|---|---|---|---|
| 5,178,833 A | 1/1993 | Covain | |
| 5,997,818 A * | 12/1999 | Hacker | G01N 21/05 210/232 |
| 6,043,880 A * | 3/2000 | Andrews | G01N 21/64 250/361 C |
| 8,981,314 B2 * | 3/2015 | Klinkhammer | G01N 21/0303 250/372 |

(Continued)

OTHER PUBLICATIONS

International Search Report and Written Opinion dated May 4, 2015 in related International Patent Application No. PCT/CA2014/050818.

*Primary Examiner* — Samuel P Siefke
(74) *Attorney, Agent, or Firm* — Eric L. Lane; Green Patent Law

(57) ABSTRACT

A mini-fluidics cassette, for detection of at least one analyte in a sample, comprising, at least one sample inlet port, at least one reagent inlet port, at least one outlet port, at least one channel extending between said at least one sample inlet port and said at least one outlet port, at least one insertion port for a fiber optic cable light source, at least one insertion port for a fiber optic cable spectrophotometer distant said at least one insertion port for a fiber optic cable light source, wherein said at least one insertion port for a fiber optic cable light source and said at least one insertion port for a fiber optic cable spectrophotometer forms part of the at least one channel, and is proximate said at least one outlet port and forms at least one reading cell/path length for light from said fiber optic cable light source to said fiber optic cable spectrophotometer port.

12 Claims, 6 Drawing Sheets

(51) Int. Cl.
  *B01F 13/00* (2006.01)
  *G01N 21/05* (2006.01)
  *G01N 21/78* (2006.01)
(52) U.S. Cl.
  CPC ............ *G01N 21/05* (2013.01); *G01N 21/78* (2013.01); *B01F 2215/0037* (2013.01); *B01L 2200/12* (2013.01); *B01L 2300/0654* (2013.01); *B01L 2300/0816* (2013.01); *B01L 2300/0867* (2013.01); *B01L 2300/0883* (2013.01); *B01L 2400/0487* (2013.01); *G01N 2201/08* (2013.01)
(58) Field of Classification Search
  CPC ..... B01L 2300/0867; B01L 2300/0816; B01L 2300/0654; B01F 13/0059; B01F 5/0647; B01F 2215/0037; G01N 21/78; G01N 21/05; G01N 2201/08
  See application file for complete search history.

(56) References Cited

U.S. PATENT DOCUMENTS

| | | | |
|---|---|---|---|
| 2003/0151744 A1 | 8/2003 | Fernando et al. | |
| 2004/0189311 A1* | 9/2004 | Glezer | B01L 3/5027 324/444 |
| 2005/0113657 A1 | 5/2005 | Alarcon et al. | |
| 2010/0297601 A1 | 11/2010 | Xu | |
| 2013/0302791 A1* | 11/2013 | Cramer | C12N 15/1013 435/6.1 |

* cited by examiner

MINI-FLUIDICS CASSETTE FOR COLORIMETRIC NUTRIENT ANALYSIS AND A METHOD OF USING SAME

FIELD

This relates to the quantification of dissolved nutrients in water by use of a mini-fluidics cassette for colorimetric analysis with minimal sample volume for measurement of dissolved nutrients in the field.

BACKGROUND

Nutrient analyses are a broad need in environmental science, with many agencies engaged in measurement of parameters of analytes, such as, but not limited to, nitrate, ammonium, and phosphate concentrations. These concentrations are critically important for function of aquatic ecosystems, and are then often used as proxies for ecosystem health. As such, agencies with water quality mandates (e.g. regulatory agencies, monitoring agencies), industries operating on discharge permits (e.g. water treatment plants), environmental engineering firms, conservation authorities, and environmental scientists are all generating high volumes of nutrient concentration data.

Currently, concentrations of analytes such as nitrate, ammonium, and phosphate may be measured based on colorimetric reactions. Standard methods for colorimetric analysis of nutrients are well established and remain largely unchanged over the past 3 decades. Other methods for quantification of nutrients include ion chromatography and ion selective electrodes. In general, colorimetric analysis remains the most common mode of nutrient analysis as these methods generally offer greater sensitivity (i.e. lower detection limits) than ion chromatography and, especially, ion selective electrodes. Colorimetric methods are also generally less sensitive to interference by other ions. Finally, colorimetric analysis requires the least specialized equipment and has low barriers for entry by users, specifically the cost and required expertise are low.

Currently, the only field methods for these analyses are test kits that are semi-quantitative and do not generate research quality data. Moreover, the kits are expensive and not amenable to large sampling campaigns. Laboratory-based nutrient analysers that generate research quality data (e.g. Lachat and ion chromatography-based systems) require that samples be preserved in the field and transported to the laboratory, so data are not available immediately. Moreover, these systems are expensive preventing adoption by many potential users.

Colorimetric methods make nutrients a laboratory parameter rather than a field parameter, meaning that these methods require that samples be collected from the field, preserved on site, and processed at a later time in the laboratory. Generally, these methods also require a significant sample size (e.g. 10-50 mL of sample) and generate a commensurate volume of waste. Further, the processing of individual samples is tedious, requiring precise volumes of sample and reagents to be measured and combined for each reaction. Some similar constraints exist for ion chromatography. Samples must be preserved and transported to the laboratory, requiring later processing and generally requiring large volumes.

It would be preferable to perform nutrient analyses using smaller volumes, particularly in situations where only small volumes of sample may be collected.

It would be preferable to generate smaller volumes of waste.

Finally, it would be preferable for nutrient analyses to be a field parameter, measured on site (in the field) without the requirement to preserve and transport samples. Such processing introduces a level of uncertainty into the subsequent quantification of the analyte.

SUMMARY

According to one aspect, there is provided a mini-fluidics cassette, preferably for use in the field for nutrient analyses. In one embodiment there is provided a plurality of mini-fluidics cassettes that may be combined with existing products (such as but not limited to peristaltic pumps and fiber-optic spectrophotometers) for measurement of multiple analytes, preferably simultaneous measurement. In one embodiment, the plurality of mini-fluidics cassettes along with existing products may be used to build a multiple nutrient analyzer, preferably having at least one of the following characteristics: economical, multichannel, semi-automated. Preferably said analytes include, but are not limited to, nitrate, nitrite, ammonium, phosphate, silica, bromide, and sulfate. Said mini-fluidics cassette may be manufactured to allow for measurement of many different analytes beyond those described herein.

According to another aspect, there is provided a mini-fluidics cassette for detection of at least one analyte comprising:
  i) At least one sample inlet port;
  ii) At least one reagent inlet port;
  iii) Preferably, in one embodiment, said cassette further comprises at least one second reagent inlet port; said second reagent inlet port distant said at least one reagent inlet port;
  iv) At least one outlet port;
  v) At least one channel extending between said at least one sample inlet port and said at least one outlet port;
  vi) At least one insertion port for a fiber optic cable light source;
  vii) At least one insertion port for a fiber optic cable spectrometer distant said at least one insertion port for a fiber optic cable light source; wherein said at least one insertion port for a fiber optic cable light source and said at least one insertion port for a fiber optic cable spectrometer is part of the at least one channel, and is proximate said at least one outlet port and forms a reading cell/path length for light from said fiber optic cable light source to said fiber optic cable spectrometer port; wherein when said analyte is a nitrate, said at least one channel further comprises an inlaid cadmium channel portion between said at least one reagent inlet port and said at least second reagent inlet port.

In one embodiment, said at least one channel is serpentine.

In yet another embodiment, said at least one analyte is selected from the group consisting of nitrate, nitrite, ammonium, phosphate, silica, bromide and sulfate. In another embodiment said at least one analyte comprises at least two analytes. In another embodiment said at least one analyte is in the form of a solution, preferably an aqueous solution.

In yet another embodiment, said cassette has a defined length, width and thickness. In one embodiment said reading cell/path runs substantially the length of said cassette.

Preferably said at least one outlet port is a waste port. Preferably said defined length of said cassette is about five centimeters, said defined width is about five centimeters and said defined thickness is about at least two centimeters.

According to another aspect said mini-fluidics cassette may be manufactured of any suitable material resistant to the analytes are reagents, preferably plastic, for example but not limited to, high-density polyethylene or high-density polypropylene. According to one embodiment, the mini-fluidics cassette may be manufactured using 3D printing. According to another embodiment, the mini-fluidics cassette may be manufactured by injection moulding.

According to yet another aspect, there is provided a system for analyte analysis of a liquid, preferably water, preferably in the field, said system comprising a plurality of mini-fluidic cassettes as described herein, wherein each of said plurality of mini-fluidic cassettes is adapted for analysis of a discrete analyte allowing for the detection and quantification of said discrete analyte in said liquid without the need of a formal laboratory. Preferably said system further comprises at least one pump for pumping said liquid and at least one reagent through said channel in said cassette, preferably a peristaltic pump; and at least one spectrophotometer, preferably a fibre optic spectrophotometer, and at least one light source, preferably a fibre optic light source.

According to yet another embodiment, there is provided a mini-fluidic cassette for the automated mixing of at least one sample and at least one reagent within the cassette, integrating chemical reaction, colour development and light absorption measurement within the mini-fluidic cassette.

According to yet another embodiment, there is provided a mini-fluidic cassette wherein said reading cell is integral with said cassette and each of said insertion ports for said light source and said spectrophotometer are threaded.

According to yet another embodiment, each of said inlet ports of said at least one sample and at least one reagent and said channel have a diameter for a controlled mixing ratio of said at least one sample to said at least one reagent. Said channel further having a diameter allowing for colorimetric analysis using a small total volume of sample and reagent, preferably reducing sample size requirement and waste generation.

According to yet another embodiment, said serpentine channel increases the overall path length travelled by said at least one sample and said at least one reagent allowing for increased mixing of said at least one sample and said at least one reagent within the mini-fluidics cassette resulting in a longer period for chemical reaction and colour development of said at least one analyte with said at least one reagent further resulting in more accurate analyte detection and quantification.

According to yet another aspect there is provided a method of analyzing at least one analyte using at least one mini-fluidics cassette comprising at least one sample inlet port, at least one reagent inlet port, in one embodiment, said cassette further comprises at least a one second reagent inlet port, said second reagent inlet port distant said at least one reagent inlet port, at least one outlet port, at least one channel extending between said at least one sample inlet port and said at least one outlet port, at least one insertion port for a fiber optic cable light source, at least one insertion port for a fiber optic cable spectrophotometer distant said at least one insertion port for a fiber optic cable light source, wherein said at least one insertion port for a fiber optic cable light source and said at least one insertion port for a fiber optic cable spectrophotometer forms part of the at least one channel, and is proximate said at least one outlet port forming a reading cell/path length for light from said fiber optic cable light source to said fiber optic cable spectrophotometer port, said method comprising the steps of:

1) introducing the at least one sample containing at least one analyte;
2) introducing at least one reagent;
3) contacting the at least one analyte with the at least one reagent;
4) conveying said contacted at least one analyte and at least one reagent through said mini-fluidics cassette;
5) illuminating said contacted at least one analyte and at least one reagent with said fibre optic cable light source; and
6) measuring absorbance of said light by said contacted at least one analyte and at least one reagent with said fibre optic cable spectrophotometer.

According to another embodiment, the at least one sample has at least one analyte selected from the group consisting of nitrate, nitrite, ammonium, phosphate, silica, bromide and sulfate. Preferably, the at least one analyte is in the form of a solution, most preferably an aqueous solution.

According to another embodiment, the contacted at least one analyte and at least one reagent preferably is conveyed through said cassette using a pump. Most preferably said pump is a peristaltic pump.

Further and other embodiments will become apparent to the skilled person.

DETAILED DESCRIPTION OF THE PREFERRED EMBODIMENTS

Figure 1:
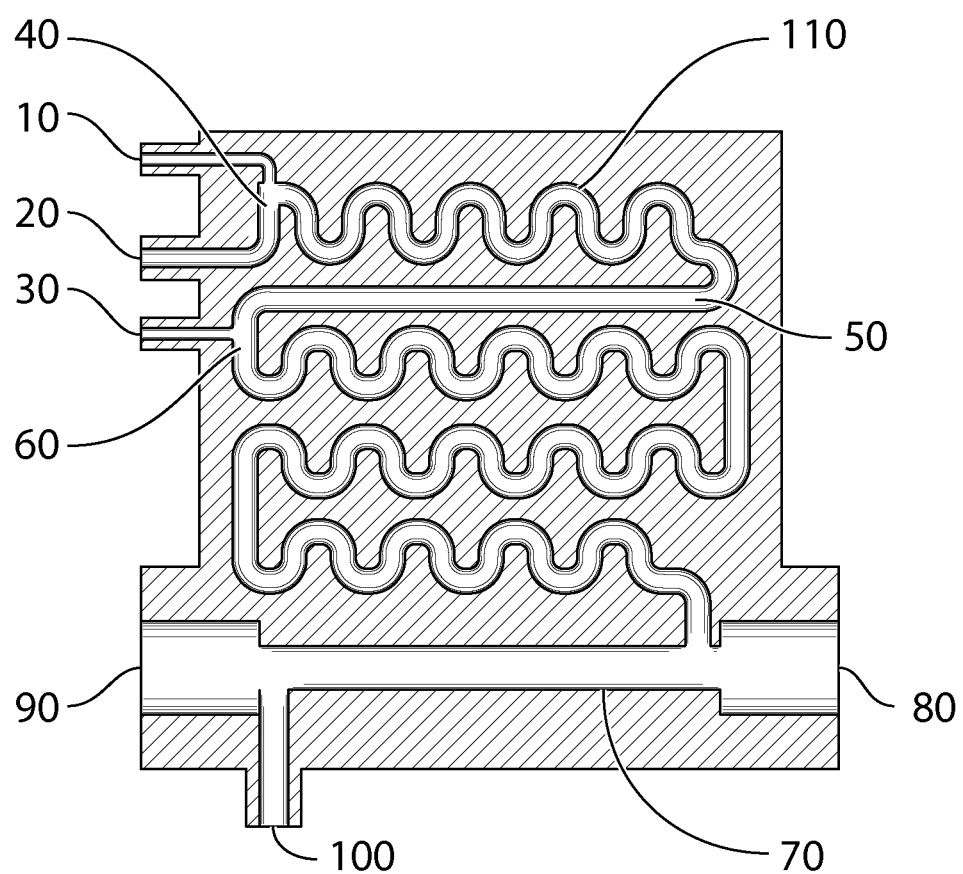
FIG. 1 is a cross sectional view of a mini-fluidic cassette specific to nitrate analysis

Referring to FIG. 1, there is provided a cross sectional view of a cassette specific to nitrate analysis of a liquid sample, providing for automated mixing of sample and reagents, and in-cassette measurement of light absorbance. There is provided a sample inlet port 10, a first reagent (buffer) inlet port 20, a second reagent inlet port 30, a first confluence zone 40 for sample and buffer, a channel for inlaid cadmium wire 50, a second confluence zone 60 for second reagent and combined sample/buffer, a reading cell/path-length for light from fiber-optic source to reading fiber 70, an insertion port for fiber-optic cable from light source 80, an insertion port for fiber-optic cable connected to spectrophotometer 90 (See FIG. 5), and an outlet port (to waste) 100. The cassette has a channel 110 to allow the sample from sample inlet port 10, first reagent (buffer) from first reagent inlet port 20 and second reagent from second reagent inlet port 30 to mix and travel through channel 110, through reading cell/path length 70 allowing a reading to be taken and sent to the spectrophotometer and out waste port 100. In this embodiment, the channel 110 is serpentine other than the inlaid cadmium wire channel 50 and reading cell/path length 70. In this manner, mixing of the sample with the reagents is maximized and sufficient transit time through the cassette is provided for chemical reaction and colour development.

In this embodiment, the cadmium wire channel 50 and the reading cell/path length 70 runs the substantial length of the cassette allowing for colour development.

Figure 2:
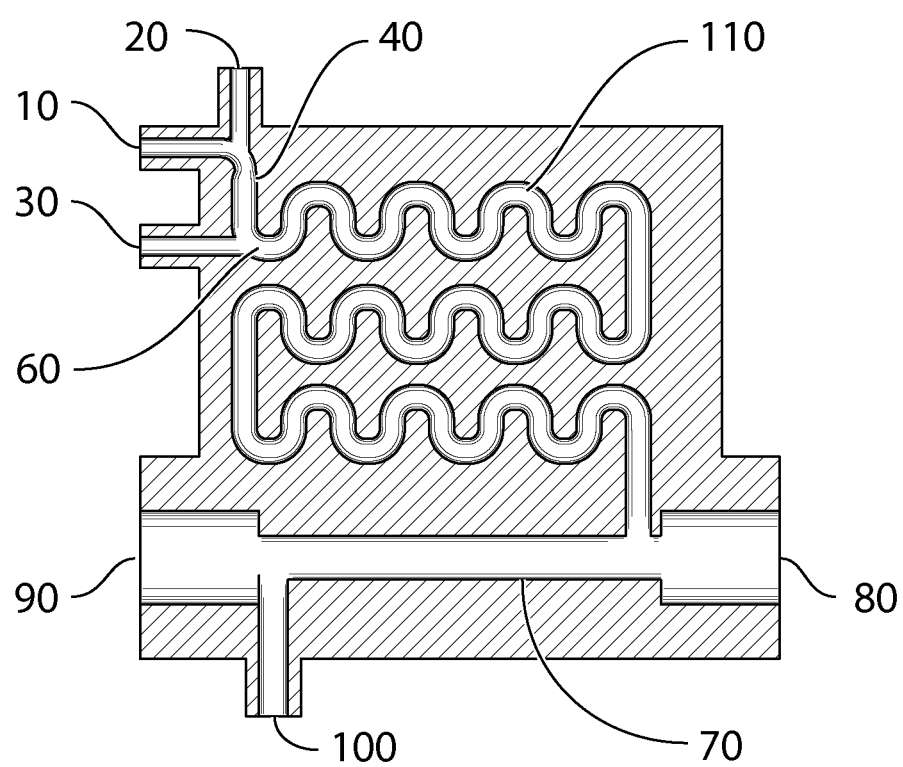
FIG. 2 is a cross sectional view of a mini-fluidic cassette specific to ammonium analysis

Referring to FIG. 2, there is provided a cross sectional view of a cassette specific to ammonium with similar elements as the cassette of FIG. 1 except for the lack of a cadmium wire inlay section along the channel. In all respects the cassette of FIG. 2 functions in a similar manner as that described in FIG. 1, except it is specific to ammonium and the sample inlet port 10 and first reagent inlet port 20 meet at a first confluence zone 40 and said mixed sample then travels past a second reagent inlet port 30 to a second confluence zone 60 prior to entering the serpentine channel 110.

Figure 3:
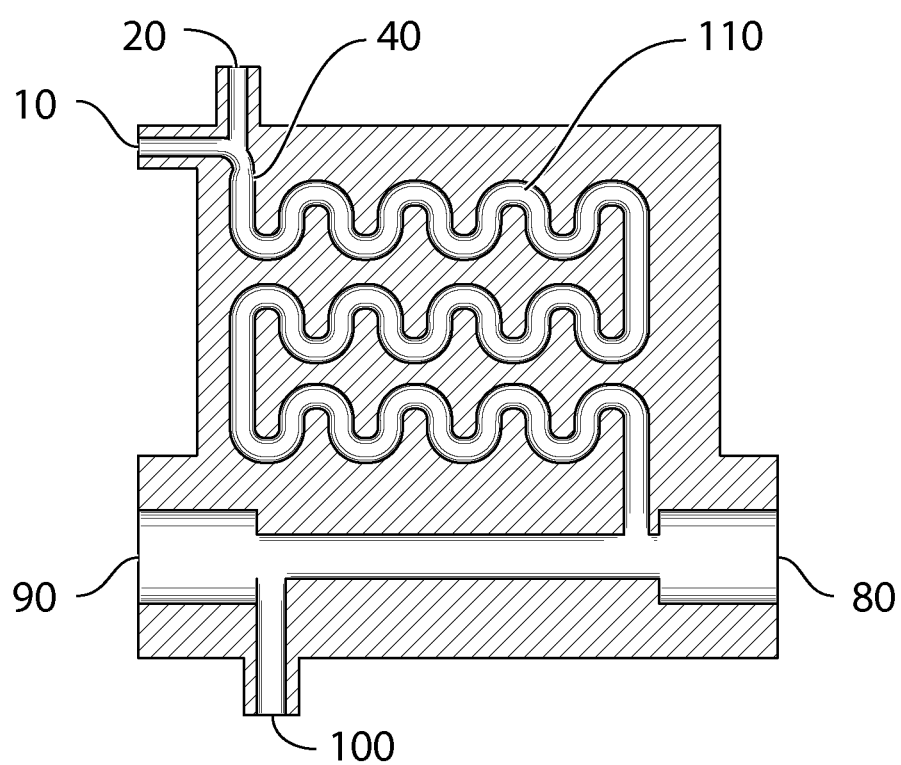
FIG. 3 is a cross sectional view of a mini-fluidic cassette specific to phosphate analysis

Referring now to FIG. 3, there is provided a cross sectional view of a cassette specific to phosphate with similar elements as the cassette of FIG. 1 except for the lack of a cadmium wire inlay section along the channel and there is a single reagent inlet port 20. In all respects the cassette of FIG. 3 functions in a similar manner as that described in FIG. 1, except it is specific to phosphate.

Figure 4:
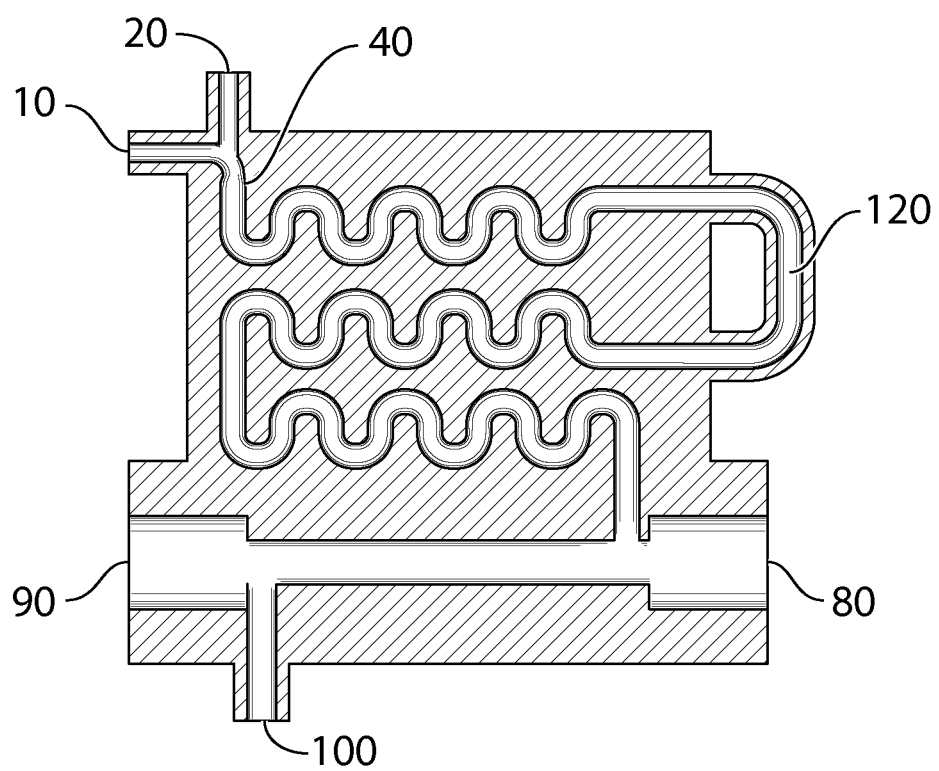
FIG. 4 is a cross sectional view of a mini-fluidic cassette specific to sulfate analysis

Referring now to FIG. 4, there is provided a cross sectional view of a cassette specific to sulfate with similar elements as the cassette of FIG. 3 except for the lack of a cadmium wire inlay section along the channel and the channel extends outside of the cassette perimeter for in-line insertion of a cartridge 120 containing an exchange resin for removal of potentially-interfering anions. In all respects the cassette of FIG. 4 functions in a similar manner as that described in FIG. 3, except it is specific to sulfate.

Figure 6:
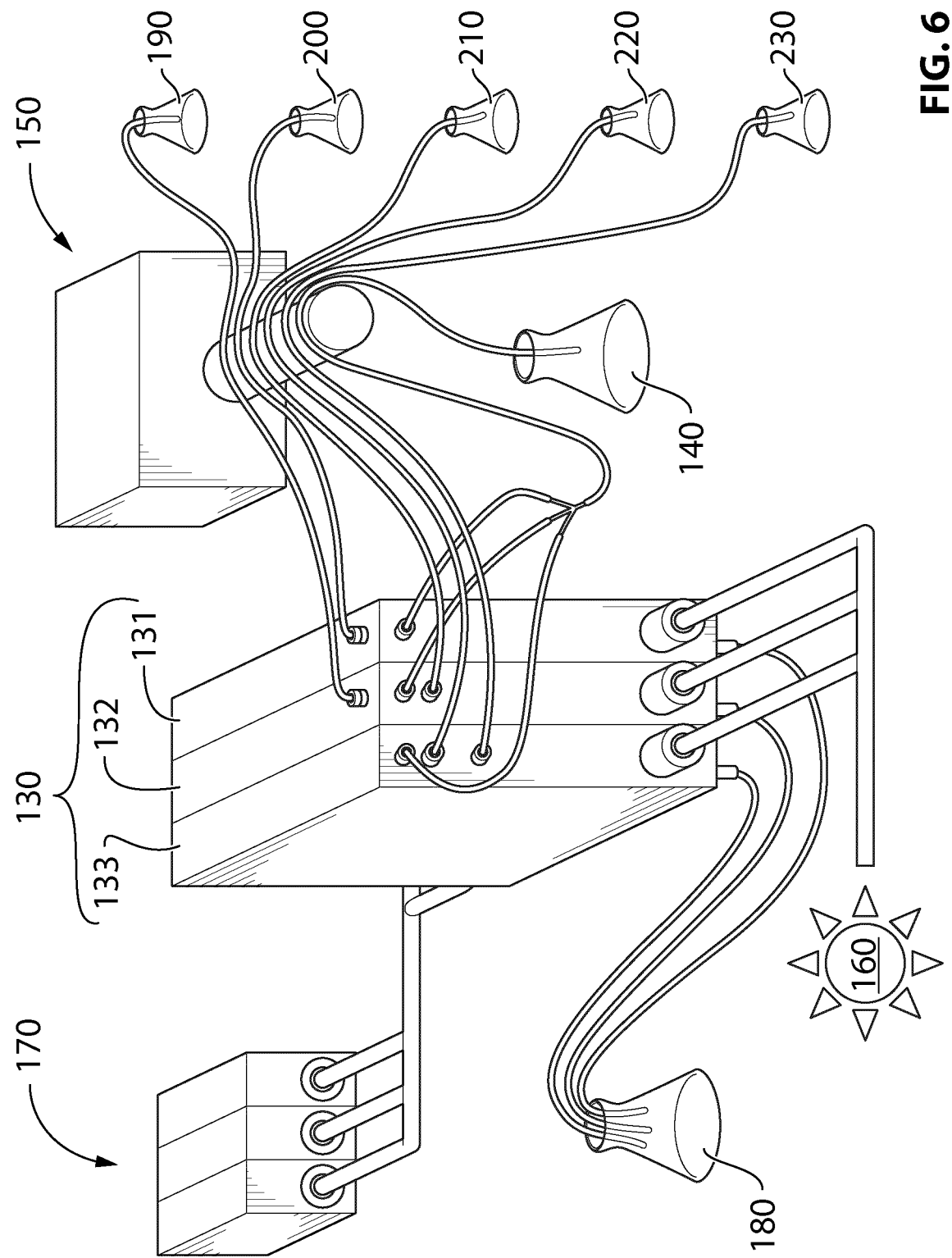
FIG. 6 is a perspective view of a system comprising a plurality of mini-fluidic cassettes analyzing a sample for a plurality of analytes

Referring now to FIG. 6, there is provided a perspective view of a system comprising a plurality of mini-fluidic cassettes analyzing a sample for a plurality of analytes. In this depiction, three mini fluidics cassettes 130, one for phosphate analyte 131, one for ammonium analyte 132 and one for nitrate analyte 133, each receive a portion of sample volume 140 via a multi channel peristaltic pump 150, each are connected to a fiber optic light source 160 and multichannel fiber optic spectrophotometer 170 and each are connected to a waste disposal unit 180. The nitrate cassette receives reagents D 220 and E 230, ammonium cassette receives reagents B 200 and C 210, and the phosphate cassette receives reagent A 190, each reagent being specific to the desired analyte to be analyzed.

In standard colorimetric analyses, specific analytes in a water sample react with chemical reagents to form coloured products (dyes). The amount of dye produced is proportional to the amount of the analyte, and may be quantified using spectrophotometry.

The cassettes described herein automate the mixing of water samples and chemical reagents used in routine colorimetric nutrient analyses, and the cassettes each have an embedded reading cell for measurement of light absorbance by the produced dyes. The reading cell portion of the cassette has ports for connection of a fiber optic light source and a reading fiber that connects to a spectrophotometer.

Figure 5:
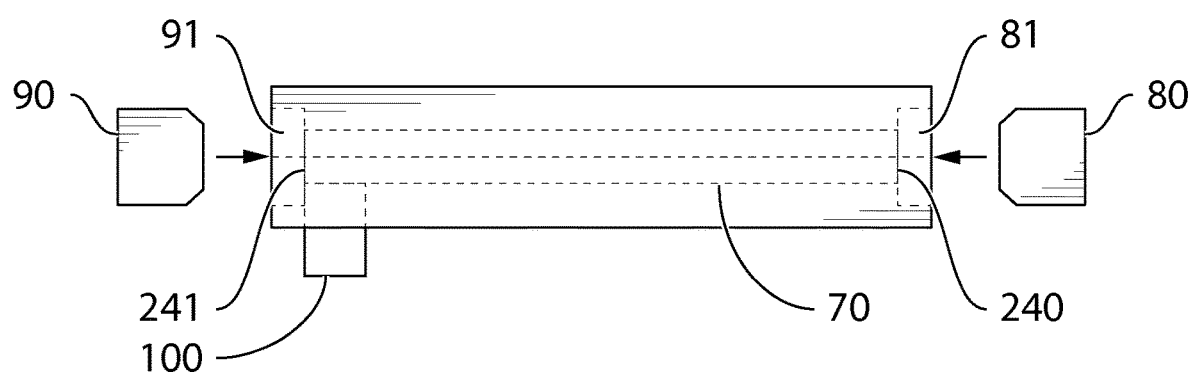
FIG. 5 is a cross sectional view of the reading cell/path-length of a mini-fluidic cassette

Each cassette operates as a flow-through cell. The cassette contains inlet ports and a serpentine channel (having a diameter in the range of <1-5 mm) that runs throughout the cassette. The diameter of each port determines the cross sectional area of the channel, and therefore the volume of sample or reagent passing through the channel in a given interval. The diameters, thus, control mixing ratios to optimize dye production. The ports introduce water samples and reagents. The sample and reagents are combined and mixed within the serpentine channels. The mixing enhances chemical reaction between analytes in the water sample and the reagents. The serpentine channel increases the total pathlength of the combined sample/reagent stream increasing time for color development. The sample flows through the reading cell. As best seen in FIG. 5, a beam of focused light passes through the glass window 240 at one end of the cell, through the sample (in this embodiment a 4 cm path-length) and through a glass window 241 at the opposite end of the cell. The light source is an optical fiber inserted into a threaded port 81 at one end of the cell. A second optical fiber inserted into a threaded port 91 on the opposite end of the reading cell transmits light to spectrophotometer. The absorption of light as it passes through the sample is recorded and may be used to quantify the dye produced within the sample, which is proportional to the analyte concentration. The sample then passes from the reading cell to waste through an exit port 100.

In a preferred embodiment each cassette is manufactured of plastic (e.g. HDPP or HDPE). Manufacturer may use 3D printing or injection molding or any other suitable process. The cassette may be produced as a solid piece or in mirrored halves to allow inlaying of a reactant material (e.g. cadmium wire for nitrate reduction) within the fluid channel. If manufactured in mirrored halves, the halves may be glued together with an adhesive appropriate for the material. When manufactured, the channel that comprises the reading cell is continuous with the fiber optic insertion ports. A tap is used to thread the ports for insertion of optical fiber collimating lenses. Circular glass cover slips (5-8 mm diameter) are then inserted into the threaded port of each reading cell and attached to the shoulder created by the narrowing of the channel to the reading cell. This creates a window on either end of the reading cell that physically separates the reading cell from the fiber optic ports (as best seen in FIG. 5).

In use, a multichannel peristaltic pump may be used to introduce the water sample and reagents to the cassette. Use of a multichannel pump and a multichannel fiber optic spectrophotometer allows the use of several cassettes in parallel for simultaneous measurement of a variety of analytes (e.g. nitrate, ammonium, phosphate, silica, sulfate, bromide), as best seen in FIG. 6.

The following are examples of the mini-fluidics cassettes and their use in analysis Example 1—Nitrate Cassette The nitrate cassette includes: a sample inlet port, 0.1 cm diameter, buffer inlet port, 0.18 cm diameter, colour reagent inlet port, 0.09 cm diameter, threaded port for fiber optic cable insertion, connection to spectrophotometer, threaded port for fiber optic cable insertion, light source, waste outlet port, 0.25 cm diameter, and channel for inlay of cadmium wire.

The cassette was produced by 3D printing in high density polyethylene. The cassette was printed in two mirrored halves and sealed using HPDE adhesive (Reltek's BONDiT A-43) to attach the two halves of each cassette, although other methods of bonding (e.g. chemical etching with use of adhesives, melting) may be used. An 8 mm diameter glass cover-slip was inserted into each fiber optic port.

A multichannel peristaltic pump is used to introduce a water sample and buffer (ammonium chloride-EDTA solution) through sample inlet port and buffer inlet port, respectively. The water sample and the buffer are mixed in a 1:3 ratio and pass through the serpentine channel to facilitate mixing. The mixed sample then passes through a channel containing a fine copperized cadmium wire to reduce nitrate to nitrite. Colour reagent (sulfanilamide/N-1-naphthylethylenediamine dihydrochloride solution) is added to the sample through colour reagent port, using another channel of the peristaltic pump. The sample passes through serpentine channels to mix the combined sample and provide time for a dye-producing chemical reaction between nitrite and sulfanilamide/N-1-naphthylethylenediamine dihydrochloride. The nitrite produced by reduction on the cadmium wire is diazotized with sulphanilamide, and coupled with N-(1-naphthyl)-ethylenediamine dihydrochloride to form a red azo dye. The sample then enters a reading cell with a 4 cm path-length. A fiber optic light source is inserted into a threaded port. Light passes through a glass window sealing the end of the reading cell near the light inlet port, through the sample in the reading cell, and through a second glass window sealing the far end of the reading cell. An optical fiber is inserted into a threaded port, conveying light to a multichannel spectrophotometer. The spectrophotometer quantifies light absorbed at 543 nm. The absorption of light at 543 nm is proportional to the amount of dye, which is, in turn, proportional to the original concentration of nitrate (+nitrite).

Peristaltic pump speed may be controlled to increase or decrease reaction time, depending on sensitivity required versus speed of analysis. The minimum sample volume required for analysis is ~650 µL. The minimum buffer volume required is ~2 mL, and the minimum required volume of sulfanilamide/N-1-naphthylethylenediamine dihydrochloride solution is ~600 µL, creating a total waste per sample of ~3.3 mL.

Procedure:

Step 1—Copperizing cadmium wire: hydrochloric acid is run through cassette for a minimum of 5 minutes. This is then followed by running copper sulfate solution through the cassette for 10 minutes, followed by EDTA buffer for 5 minutes.

Step 2—Conditioning wire: run 100 µM potassium nitrate solution through the cassette for 5 minutes, followed by EDTA buffer for 5 minutes.

Step 3—Connect tubing: connect peristaltic tubing to ports (2.10 mm i.d. to ports 10 and 30, 2.79 mm i.d. to port 20).

Step 4—Run samples: pump water sample into port 10, EDTA buffer into port 20 and sulphanilamide/N-1-naphthylethylenediamine dihydrochloride solution into port 30.

Step 5—Record absorbance: once waste begins to exit through outlet port, stop pump and allow 5-10 minutes for colour development and then record absorbance from fiber optic spectrophotometer.

Step 6—Flush cassette: flush between samples with EDTA buffer (into port 20) and distilled water into ports 10 and 30.

Step 7—Storage: after analyzing samples, do a final flush of cassette with EDTA buffer and store cassette filled with buffer.

Reagents:

Sulphanilamide/N-1-naphthylethylenediamine dihydrochloride solution: To approximately 800 mL of reagent distilled water (deionized water may also be used), add, while stirring, 100 mL concentrated, phosphoric acid (CASRN 7664-38-2), 40 g sulfanilamide (CASRN 63-74-1) and 2 g N-1-naphthylethylenediamine dihydrochloride (CASRN 1465-25-4) reagent grade. Stir until dissolved and dilute to 1 L. Store in brown bottle and keep in the dark when not in use. This solution is stable for several months.

EDTA buffer solution: Dissolve 85 g of reagent grade ammonium chloride (CASRN 12125-02-9) and 0.1 g of disodium ethylenediamine tetracetate (CASRN 6381-92-6) in 900 mL of distilled water. Adjust the pH to 9.1 for preserved or 8.5 for non-preserved samples with concentrated ammonium hydroxide (CASRN 1336-21-6) and dilute to 1 L. Add 0.5 mL Brij-35 (CASRN 9002-92-0).

Comparison with APHA (1997) Standard Method 4500-$NO_3^-$E—cadmium reduction column: Nitrate was analyzed using a cassette as described above, and also using APHA method 4500-$NO_3^-$E. For each method, a standard curve was generated using working standards containing 0, 5, 10, 15, 20, and 25 µM $NO_3^-$. Samples were collected from 5 different water sources. For quality control, each sample was analyzed with and without a nitrate spike (10 µM) and a known standard (5 µM) was analyzed after every 5 samples. The detection limit for each method was calculated as 3 times the minimum nitrate concentration necessary to generate a signal above background (0 µM nitrate). The two methods had comparable limits of detection for nitrate (3.0 µM for cassette method, 3.7 µM for method 4500-$NO_3^-$E). The cassette had an average percent recovery in the five spiked samples of 100%, while method 4500-$NO_3^-$E had an average percent recoveries of 197%, suggesting the cadmium reduction column was inefficient in reducing nitrate to nitrite at low concentrations. Calculated concentrations in control samples were similar between methods (4.27 µM for cassette method, 5.33 µM for method 4500-$NO_3^-$E. Generally, the cassette yielded similar results to the traditional wet chemistry methods while resulting in much less waste (~2 mL per sample versus ~20 mL per sample).

Example 2—Ammonium Cassette

Similar to Example 1, a multichannel peristaltic pump is used to introduce a water sample, phenol/nitroprusside solution, and oxidizing solution through 10, 20, and 30 (FIG. 2), respectively. Phenol reacts with ammonium in the water sample and hypochlorite in the oxidizing solution. The reaction, catalyzed by nitroprusside, produces indophenol, an intensely blue compound. The combined sample enters reading cell 70 with a 4 cm path-length. Light absorbance at 640 nm is measured using a fiber optic light source and spectrophotometer. The absorption of light at this wavelength is proportional to the amount of indophenol, which is, in turn, proportional to the original concentration of ammonium in the sample.

Peristaltic pump speed can be controlled to increase or decrease reaction time, depending on sensitivity required versus speed of analysis. The minimum volume of sample, phenol/nitroprusside solution, and oxidizing solution required for analysis is ~1.2 mL, creating a total waste per sample of <3.6 mL.

Procedure:

Step 1—Connect tubing: connect peristaltic tubing to ports (2.79 mm i.d. to ports 10, 20, and 30).

Step 2—Run samples: pump water sample into port 10, phenol/nitroprusside solution into port 20, oxidizing solution into port 30.

Step 3—Record absorbance: once waste begins to exit through outlet port, stop pump and allow 5-10 minutes for colour development and then record absorbance from fiber optic spectrophotometer.

Step 4—Flush cassette: flush between samples with distilled water.

Step 5—Storage: after analyzing samples, do a final flush of cassette with distilled water, then remove the pump tubing from water and pump air through the cassette. Store dry.

Reagents:

Phenol/nitroprusside solution: combine phenol solution and sodium nitroprusside solution in 1:1 ratio. Dilute 10-fold using distilled water. Prepare fresh daily.

Phenol solution: mix 11.1 mL liquefied phenol (>=89%) with 95% v/v ethyl alcohol to a final volume of 100 mL. Prepare weekly.

Sodium nitroprusside solution: dissolve 0.5 g sodium nitroprusside in 100 mL deionized water. Store in amber bottle for up to 1 month.

Oxidizing Solution: combine alkaline citrate solution with sodium hypochlorite (bleach) at 4:1 ratio. Dilute 10-fold using distilled water. Prepare fresh daily.

Alkaline Citrate Solution: dissolve 100 g trisodium citrate and 5 g sodium hydroxide in deionized water. Dilute to 500 mL.

Comparison with APHA (1997) Standard Method 4500-$NH_3$ F—phenate method:

Ammonium was analyzed using a cassette as described above, and also using APHA method 4500-$NH_3$ F. For each method, a standard curve was generated using working standards containing 0, 5, 10, 15, 20, and 25 µM $NH_4^+$. Samples were collected from 5 different water sources. For quality control, each sample was analyzed with and without an ammonium spike (10 µM) and a known standard (10 µM) was analyzed after every 5 samples. The detection limit for each method was calculated as 3 times the minimum ammonium concentration necessary to generate a signal above background (0 µM ammonium). The standard method had lower limits of detection (2.25 µM for cassette method, 1.1 µM for method 4500-$NH_3$ F). Calculated concentrations in control samples were similar between methods (8.4 µM for cassette method, 9.6 µM for method 4500-$NH_3$ F. Generally, the cassette yielded lower calculated sample concentrations than method 4500-$NH_3$ F, however this can be improved with increased length of the serpentine channel to increase reaction time before the sample reaches the reading cell. The cassette method resulted in less waste generation than method 4500-$NH_3$ F (~2 mL per sample versus ~5.5 mL per sample).

Example 3—Phosphate Cassette

Similar to Example 1, a multichannel peristaltic pump is used to introduce a water sample and a color reagent through 10 and 20 (FIG. 3), respectively. The color reagent contains ammonium molybdate and potassium antimonyl tartrate, which react with ortho-phosphate in the water sample, producing phosphomolybdic acid. Ascorbic acid, another constituent of the colour reagent, reduces the phosphomolybdic acid to molybdenum blue. The combined sample then enters reading cell 70 with a 4 cm path-length. Light absorbance at 880 nm is measured using a fiber optic light source and spectrophotometer. The absorption of light at this wavelength is proportional to the amount of dye, which is, in turn, proportional to the original concentration of ortho-phosphate.

Peristaltic pump speed can be controlled to increase or decrease reaction time, depending on sensitivity required versus speed of analysis. The minimum sample volume required for analysis is ~1.3 mL, and the minimum color reagent volume required is ~1.3 mL, creating a total waste per sample of <2.5 mL.

Procedure:

Step 1—Connect tubing: connect peristaltic tubing to ports (2.79 mm i.d. to ports 10 and 20).

Step 2—Run samples: pump water sample into port 10, color reagent into port 20.

Step 3—Record absorbance: once waste begins to exit through outlet port, stop pump and allow 5-10 minutes for colour development and then record absorbance from fiber optic spectrophotometer.

Step 4—Flush cassette: flush between samples with distilled water.

Step 5—Storage: after analyzing samples, do a final flush of cassette with distilled water, then remove the pump tubing from water and pump air through the cassette. Store dry.

Reagents:

Color Reagent: Combine 10 mL of reagent: 5 mL 5N $H_2SO_4$, 0.5 mL potassium antimonyl tartrate solution, 1.5 mL $NH_4$ molybdate solution, 3 mL ascorbic acid solution. Dilute to 100 mL with distilled water.

Potassium Antimonyl: dissolve 1.3715 g K(SbO)$C_4H_4O_6 \times 4H_2O$ into 400 mL distilled water. Dilute to 500 mL with distilled water.

Ammonium Molybdate Solution: dissolve 20 g $(NH_4)_6M_{O7}O_{24}$ into 400 mL distilled water. Dilute to 500 mL with distilled water.

Ascorbic Acid: dissolve 1.76 g ascorbic acid into 100 mL distilled water.

Comparison with APHA (1997) Standard Method 4500-P E—molybdate/ascorbic acid method: Phosphate was analyzed using a cassette as described above, and also using APHA method 4500-P E. For each method, a standard curve was generated using working standards containing 0, 5, 10, 15, 20, and 25 µM $PO_4^{3-}$. Samples were collected from 5 different water sources. For quality control, each sample was analyzed with and without a phosphate spike (10 µM) and a known standard (10 µM) was analyzed after every 5 samples. The detection limit for each method was calculated as 3 times the minimum phosphate concentration necessary to generate a signal above background (0 µM phosphate). The cassette method had a lower limit of detection (<0.1 µM for cassette method, 0.3 µM for method 4500-P E). Percent recoveries in spiked samples were comparable between methods (average recovery 111% for cassette method, 106% for method 4500-P E). Generally, the cassette yielded slightly higher calculated sample concentrations than method 4500-P E. The cassette method resulted in less waste generation than method 4500-P E (~2 mL per sample versus ~5.5 mL per sample).

As many changes can be made to the preferred embodiment of the invention without departing from the scope thereof; it is intended that all matter contained herein be considered illustrative of the invention and not in a limiting sense. The scope of the claims should not be limited by the preferred embodiments set forth in the examples, but should be given the broadest interpretation consistent with the description as a whole.

The invention claimed is:

1. A system for analysis of at least one analyte in a liquid, said system comprising:
   i) At least one mini-fluidics cassette comprising:
      At least one sample inlet port;
      At least one reagent inlet port;
      At least one outlet port;
      At least one channel extending between said at least one sample inlet port and said at least one outlet port;
      At least one insertion port for a fiber optic cable light source; and At least one insertion port for a fiber optic cable spectrophotometer distant said at least one insertion port for a fiber optic cable light source; wherein said at least one insertion port for a fiber optic cable light source and said at least one insertion port for a fiber optic cable spectrophotometer forms part of the at least one channel, and is proximate said at least one outlet port and forms at least one reading cell/path length for light from said fiber optic cable light source to said fiber optic cable spectrophotometer port; wherein when said analyte is a nitrate, said at least one channel further comprises an inlaid cadmium channel portion between said at least one reagent inlet port and said at least second reagent inlet port;

ii) at least one pump for pumping said liquid and at least one reagent through said cassette;

iii) at least one light source; and iv) at least one spectrophotometer.

2. The system of claim 1 wherein the at least one mini-fluidics cassette comprises a plurality of mini-fluidics cassettes;

i) wherein each of said plurality of mini-fluidics cassettes is adapted for analysis of a discrete analyte allowing for the detection and quantification of said discrete analyte in said liquid.

3. The system of claim 1 further comprising at least one second reagent inlet port; said second reagent inlet port distant said at least one reagent inlet port.

4. The system of claim 1 wherein said at least one channel is serpentine.

5. The system of claim 1 wherein said at least one analyte is selected from the group consisting of nitrate, nitrite, ammonium, phosphate, silica, bromide and sulfate.

6. The system of claim 1 wherein said at least one analyte comprises at least two analytes.

7. The system of claim 1 wherein said at least one analyte is in the form of a solution.

8. The system of claim 1 wherein said reading cell/path runs substantially the length of said cassette.

9. The system of claim 1 wherein said at least one outlet port is a waste port.

10. The system of claim 1 wherein said cassette is manufactured of a material resistant to said at least one analyte.

11. The system of claim 1 wherein said cassette is manufactured of a material selected from the group consisting of plastic, high-density polyethylene, high-density polypropylene and combinations thereof.

12. The system of claim 1 wherein said cassette is manufactured by 3D printing or injection moulding.

* * * * *